United States Patent
Schneider et al.

[11] Patent Number: 6,116,088
[45] Date of Patent: Sep. 12, 2000

[54] METHOD OF OPERATING A MACHINE FOR STRESS RELIEVING WORKPIECES

[75] Inventors: Dietmar Schneider, Schlangenbad, Germany; Christian Vava, Worchester, Mass.

[73] Assignee: VSR Martin Engineering GmbH, Schlangenbad, Germany

[21] Appl. No.: 09/122,025

[22] Filed: Jul. 24, 1998

[30] Foreign Application Priority Data

Jul. 24, 1997 [EP] European Pat. Off. ............. 97112748

[51] Int. Cl.[7] .................................................. G01H 13/00
[52] U.S. Cl. ........................................................ 73/579
[58] Field of Search ..................... 73/579, 577; 148/508, 148/558

[56] References Cited

U.S. PATENT DOCUMENTS

| | | | |
|---|---|---|---|
| 3,622,404 | 11/1971 | Thompson | 148/558 |
| 3,677,831 | 7/1972 | Pezaris et al. | 148/12.9 |
| 4,001,053 | 1/1977 | Igisu | 148/558 |
| 4,446,733 | 5/1984 | Okubo | 73/579 |
| 4,718,473 | 1/1988 | Musschoot | 164/132 |
| 4,823,599 | 4/1989 | Schneider | 73/579 |
| 4,968,359 | 11/1990 | Hebel et al. | 148/12.9 |
| 6,026,687 | 2/2000 | Jury | 73/582 |

FOREIGN PATENT DOCUMENTS

| | | |
|---|---|---|
| 0261273 | 3/1988 | European Pat. Off. . |
| 2088268 | 6/1982 | United Kingdom . |
| 93-18376 | 9/1993 | WIPO . |

*Primary Examiner*—Richard A. Moller
*Attorney, Agent, or Firm*—Sidley & Austin

[57] ABSTRACT

A method is disclosed for stress relieving workpieces, having the steps of causing the workpiece to vibrate due to selected revolution values of a vibrator and making the selection of the revolution values on the basis of a measurement revealing the vibration behavior of the work piece. The workpiece is excited with revolutions of predetermined frequencies in a limited operating range and the respective response behavior associated with the excitation vibrations is measured and evaluated. In so doing, an efficiency value is determined for each excitation frequency and, with the aid of a correlation between the calculated efficiency values and conventionally selected excitation frequencies, further frequencies are selected for stress relieving the workpiece.

17 Claims, 1 Drawing Sheet

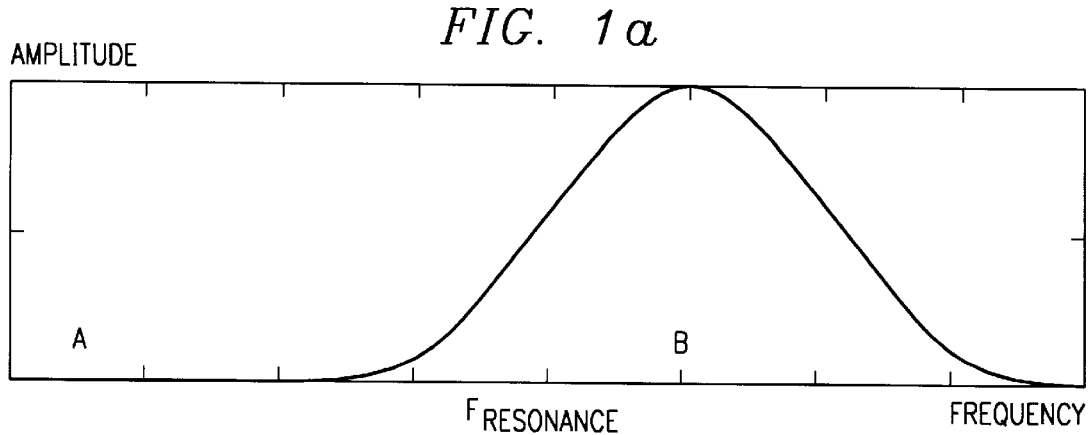
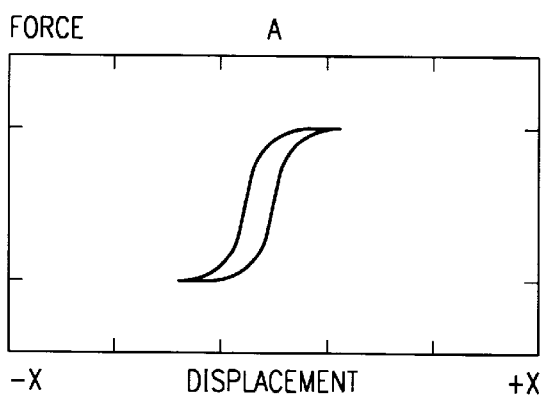
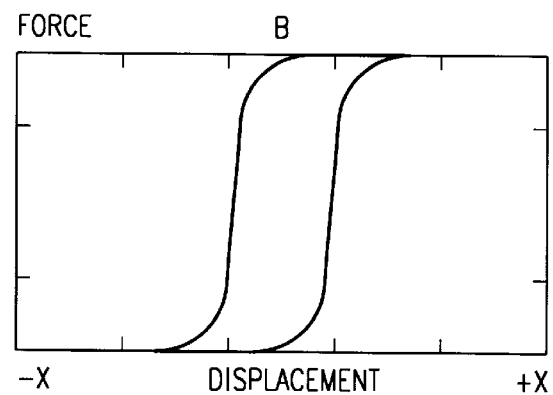
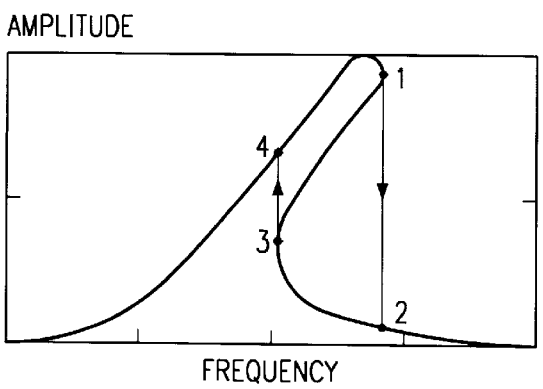
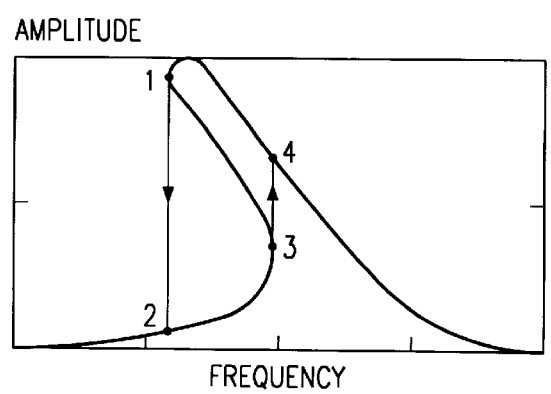

METHOD OF OPERATING A MACHINE FOR STRESS RELIEVING WORKPIECES

FIELD OF THE INVENTION

The present invention refers to a method for a machine used for stress relieving workpieces, comprising the steps of causing the workpiece to vibrate due to selected revolution values of a vibrator and making the selection of the revolution values on the basis of a measurement revealing the vibration behavior of the workpiece.

BACKGROUND OF THE INVENTION

Internal stresses in metallic workpieces can be reduced by subjecting the workpiece to vibrations causing a decrease of internal stresses.

These workpieces are normally excited with a number of revolutions in the range of from 1200 to 6000 rpm or also up to 12,000 rpm for stress relief. These numbers of revolutions correspond to excitation frequencies of 20 to 100 Hz and 200 Hz, respectively. It is, however, difficult to ascertain the excitation frequencies with which an optimum and purposeful reduction of the internal stresses can be achieved. In the publications GB 20 88 269, U.S. Pat. No. 3,677,831, U.S. Pat. No. 4,446,733 and EP 0 261 273 B1 methods are described by means of which suitable frequencies can be determined for exciting the workpieces. In the case of these methods, a test run within the operating range, which will also be referred to as macroscanning hereinbelow, is first carried out for determining at which numbers of revolutions or excitation frequencies the workpiece starts to vibrate strongly (resonant frequency). The vibration behavior is normally determined with the aid of an accelerometer which is secured to the workpiece. For eliminating the internal stresses, the workpiece is then subjected to vibrations at frequencies at which the workpiece shows resonances during the test phase. If the workpieces in question have a complicated three-dimensional structure, an acceleration value/excitation frequency diagram will normally contain so many peak values that a selection has to be made for the stress relief phase.

The method according to U.S. Pat. No. 4,446,733 only uses the harmonic vibration in the ultrasonic region for stress relief. In the case of the method according to EP 0 261 273 B1, the harmonic vibrations lying outside of the operating range are only used as a basis for calculating the excitation frequencies from the low operating frequency range. The stress relief is, consequently, only carried out with low frequencies.

It is known that the motions in the microscopic region which are necessary for stress relief are excited not directly by the excitation frequencies of the vibrator, but only by the harmonics of the excitation frequencies. When excitation frequencies have been determined previously, it has been assumed that excitation frequencies, which resulted in particularly high peak values in the test run, will also result in a particularly strong excitation of the workpiece in the microscopic region, which is the region of interest. Practical experience has, however, shown that not all the revolution values which achieved amplitude maxima in the test run will also result in a high excitation in the frequency range of interest.

BRIEF SUMMARY OF THE INVENTION

It is therefore the object of the present invention to provide a method of operating a machine for stress relieving workpieces in the case of which the workpiece is excited with vibrations of such revolution values of the vibrator which are suitable for achieving an adequate reduction of the internal stresses of the workpiece with little effort.

For this purpose, a respective efficiency value is determined for the revolution values at which maxima occur in the curve measured during the test phase, the efficiency value indicating the efficiency with which the workpiece is caused to vibrate in the frequency ranges which are of interest with regard to the stress relief process. Such an efficiency value can be determined in a particularly simple manner when the curve measured is transformed from the time domain into the frequency domain and when, subsequently, the energy of the spectral component above the fundamental is related to the total energy, i.e. the energy including the fundamental. Upon evaluating the correlation between the efficiency values and the selected revolution values, the revolution values having associated therewith the highest efficiency values are ascertained and used for the purpose of stress relieving the workpiece. The stress relief operation can in this way be carried out making use of an only very small number of excitation revolution values with the best possible stress relief result and within the shortest possible time. The improvement of the stress relief process is based on the fact that—in comparison with conventional methods—the stress relief frequencies used are only those causing an optimum excitation of the workpiece in the frequency range required for stress relief.

In accordance with a preferred embodiment, the stress relief frequencies to be used can be reduced still further and the stress relief process can be accelerated still further by using, for the purpose of stress relief, only frequencies which are not an integer multiple of some other selected excitation frequency, the frequency used for stress relieving the workpiece being only the frequency resulting in a better excitation in the frequency range of interest, i.e. the frequency used among these frequencies is the only one having associated therewith the higher efficiency value. In this way, the number of stress relief frequencies and the duration of the stress relief process can be reduced still further.

An efficiency value, for selecting the frequencies that are to be used for the stress relief process, can be rendered even more expressive by means of a more complicated calculation method. For this purpose, all efficiency values are calculated which indicate the excitation efficiency of revolution frequencies comprised in a specific range around the revolution values selected on the basis of the curve measured. This revolution range is preferably determined by taking into account all the revolution values whose amplitude does not fall below a threshold amplitude starting from a respective maximum value, the threshold amplitude being smaller than the maximum value by a predetermined factor. This factor is preferably $1/\sqrt{2}$. The efficiency values used in the case of this determination process indicate much more precisely the actual excitation achieved in the frequency range of interest, since inaccuracies occurring in the test phase and in the excitation for stress relief are compensated for. Hence, the efficiency value ascertained corresponds much better to the excitation which is actually of interest.

The stress relief process can be improved still further in that the revolution frequency used for stress relieving the workpiece is varied within a predetermined range. The width of the range corresponds preferably to the width used for calculating a mean efficiency value.

On the one hand, the mean efficiency value ascertained will, in the case of this type of stress relief, precisely correspond to the excitation frequency range used for the stress relief; on the other hand, vibrations with a correspondingly varying frequency are produced in this way in the frequency range which is relevant to the stress relief process, whereby microscopic structures having slightly varying sizes can be caused to carry out the desired motion.

In accordance with a preferred embodiment of the present method, the revolution values are also varied in the test phase within a predetermined range around the respective number of excitation revolutions continuously or in small steps, referred to hereinbelow also as microscanning, so that, within the range of variation, the excitation frequency will increase in one case and decrease in another during the excitation. An advantage of this type of excitation is that the control circuit used for setting the excitation frequency can be implemented in a simpler and less expensive manner, since the accuracy with which the revolution frequency must be set has a larger variation width and since a longer dead time, among other things, can therefore be used in the control circuit employed.

If the workpiece is purposefully excited by a non-sinusoidal periodic force in the test phase, the workpiece will be caused to vibrate not only by the fundamental but also by the respective harmonics. The percentage of desired higher excitation frequencies can clearly be increased in this way.

In accordance with an advantageous embodiment, the variation, i.e. the microscanning, within the predetermined range around the respective number of excitation revolutions is carried out repeatedly, and on the basis of the amplitude values measured during each microscanning run an average value of the measured amplitude values is formed for each of the numbers of excitation revolutions, the average value being formed separately in the direction of increasing and decreasing microscanning revolution values. This will make the measured amplitude curve much more expressive, since the influence of statistic fluctuations is reduced. In the range of a resonant amplitude, this amplitude is measured several times in the course of several microscanning runs. By calculating the variance of all measured resonant amplitudes, a parameter can be determined which indicates to what extent the resonant amplitude has varied during the excitation in the microscanning runs. A variation of the resonant amplitude during the microscanning runs in the test phase results in a larger variance value indicating the extent to which the vibration that has already been injected in the workpiece during the test phase caused a stress relief. In this way, a further efficiency value can be indicated in connection with each maximum value, the further efficiency value showing to what extent such a revolution value is suitable for a rapid stress relief of the workpiece. This efficiency value, which will be referred to as variation efficiency hereinbelow, should advantageously be formed by the quotient of the measured variance value and the measured resonant amplitude.

For determining a common efficiency value for each of the measured maximum values, the efficiency value (THD) and the variation efficiency value are connected in such a way that they mutually enhance each other. This means that, when the value of an efficiency value increases, the value of the common efficiency value will increase as well. In this way, the common efficiency value represents a combined quality criterion for each measured maximum value, the quality criterion indicating the efficiency with which suitable excitation frequencies can be injected in the workpiece by means of the respective number of excitation revolutions and the velocity with which the respective number of excitation revolutions causes a stress relief in the workpiece.

Such a connection of the energy efficiency value and of the variation efficiency value can, for example, be obtained by multiplying the two individual values.

Not all the revolution values in the range of the respective maxima of the curve measured during the test phase are equally suitable for stress relieving the workpiece. When a workpiece is caused to vibrate at specific frequencies, this can result not only in an elimination of internal stresses of the workpiece but also in an increase of the internal stresses. In order to be able to differentiate between such a stress-increasing and a stress-relieving behavior, the vibration behavior of the workpiece must be examined in an excitation frequency range around the respective revolution frequencies selected. For this purpose, the excitation frequency fluctuates in a range around the respective selected excitation frequency so as to be able to determine and to evaluate the vibration behavior of the workpiece in the case of increasing and decreasing frequencies. On the basis of the differences detected in the measured curve in the case of increasing and decreasing frequencies, a stress-increasing (hard spring behavior) and a stress-relieving (soft spring behavior) can be distinguished. The frequencies which are suitable for stress relieving the workpiece are only those exhibiting a soft spring behavior. The number of the stress-relieving frequencies which are to be used can in this way be reduced still further, and, in addition, an undesired increase in the internal stresses can be excluded.

In accordance with an advantageous embodiment, the revolution values exhibiting a hard spring behavior are additionally used for preventing revolution values, which, though they exhibit a soft spring behavior, represent an integer multiple or a divisor of one of the hard spring frequencies, from being used for the purpose of stress relief. In this way, an unintentional increase of internal stresses is avoided.

A soft spring behavior can be distinguished from a hard spring behavior. A decisive criterion for distinguishing these kinds of behavior is the characteristic occurrence of amplitude jumps in the case of increasing and decreasing excitation frequencies. A small and a big amplitude jump can occur during increasing as well as during decreasing excitation frequencies. A method evaluates which of these two jumps occurs during increasing and which during decreasing frequencies. The big amplitude jump always takes place from a big amplitude towards a small amplitude, and the small amplitude jump always takes place from a smaller amplitude towards a larger amplitude. The hard spring behavior is characterized in that the big amplitude jump takes place during increasing excitation frequencies and the small amplitude jump during decreasing excitation frequencies, whereas in the case of a soft spring behavior a small amplitude jump occurs during increasing excitation frequencies and a big amplitude jump during decreasing excitation frequencies. It can, alternatively, be examined at which excitation frequencies these amplitude jumps occur. In the case of a soft spring behavior, the big amplitude jump takes place at an excitation frequency which is lower than the excitation frequency at which the small amplitude jump takes place, in the case of a hard spring behavior, the big amplitude jump takes place at an excitation frequency which is higher than the excitation frequency at which the small amplitude jump takes place. Used individually or in combination, these two methods permit a selection of only those frequencies by means of which a real stress relief of the workpiece can be effected.

In order to avoid an undesired increase of internal stresses, the revolution values which should be excluded from use for the purpose of stress relief should not only be the revolution values that can unequivocally have assigned thereto a hard spring behavior but also all the revolution values that cannot unequivocally have assigned thereto a soft spring behavior.

For achieving a genuine stress relief, it will be advantageous to excite the workpiece not only with a fundamental frequency but also—by using a non-sinusoidal force—with a large number of harmonics for the purpose of stress relief. In accordance with a particularly advantageous embodiment, two vibrators are used simultaneously for stress relieving the workpiece. The two vibrators operate preferably with slightly different numbers of revolutions.

For eliminating the internal stresses of the respective workpiece within the shortest possible time and as completely as possible, the period of time in the course of which the workpiece is stress relieved at a specific frequency can be kept as short as possible by supervising the vibration behavior of the workpiece in addition to the above-described measures for determining the most suitable excitation frequencies. In so doing, the workpiece is caused to vibrate only as long as necessary for achieving a predetermined degree of stress relief. For this purpose, the curve measured during the relief phase is evaluated. When the amplitude curve reaches a predetermined degree of symmetry and/or a predetermined degree of flatness in the range of the excitation frequency measured, the stress relief process carried out at this frequency can be discontinued, since a stress relief of the workpiece exceeding this predetermined value is no longer necessary.

BRIEF DESCRIPTION OF THE SEVERAL VIEWS OF THE DRAWINGS

Embodiments of the present invention will be explained in detail making reference to the drawing, in which:

FIG. 1a is a frequency-amplitude diagram of the present invention;

FIG. 1b is an excitation force-displacement diagram for the excitation frequency A in FIG. 1a;

FIG. 1c is an excitation force-displacement diagram for the excitation frequency B in FIG. 1a;

FIG. 2a is a frequency-amplitude diagram for a hard spring behavior; and

FIG. 2b is a frequency-amplitude diagram for a soft spring behavior.

DETAILED DESCRIPTION OF THE INVENTION

In connection with stress-relief machines of the type discussed in the present invention, it is assumed that not all frequencies are equally suitable for stress relieving a workpiece. Normally, resonant frequencies are used as excitation vibrations. However, not even all the resonant frequencies are equally suitable. The method described in the present connection serves to ascertain the most suitable excitation frequencies.

With the aid of the analysis described in the present connection, the energetic transfer efficiency for stress relief is evaluated. The transfer efficiency is calculated on the basis of the spectral composition.

For determining the spectral response of the workpiece during a test phase, the workpiece is excited with revolution frequencies scanning the operating range continuously or such that they increase and decrease in small steps (macroscanning).

In view of the fact that the load applied to the motor shaft of the vibrator is not uniform during one revolution of the shaft, the instantaneous excitation applied to the workpiece has an instantaneous frequency value that varies around an average. In this way, the frequency value excited is not only one special frequency value but a range around the mean angular velocity is scanned. Also in the case of conventional devices a range around the mean angular velocity is scanned even if it is intended to operate the vibrator with a constant number of revolutions, the excitation taking place being then much broader. Conventional methods are not capable of utilizing this frequency broadening in an advantageous manner.

In accordance with a different embodiment, the workpiece is excited by a blow whose frequency spectrum extends over all frequencies. The vibration behavior of the workpiece is determined by evaluating the impulse response which is converted into a spectral representation for further processing.

When the workpiece is excited according to the first embodiment, the revolution frequency scans the operating frequency range continuously or such that it increases and decreases in small steps. Such a variation of the excitation frequency (microscanning) takes place much faster than the variation occurring in the case of macroscanning, but its variation width is much smaller. At the same time, the respective instantaneous acceleration of the workpiece is measured and recorded. For this purpose, an accelerometer is attached to the workpiece at the point which is most suitable for transmitting the frequencies to be evaluated.

It will be advantageous to use a 3D acceleration sensor for the accelerometer. The use of such a 3D accelerometer has several advantages: during the test phase, dangerous peak values can be detected, which originate from mechanical resonances that are determined by the physical dimensions of the workpiece. These mechanical resonances differ from the rectangular ones of the motor shaft and of the workpiece surface to which the vibrator is secured. Such resonances cannot be detected by means of an 1D acceleration sensor, whereby the cooperation of the motor and the vibrator is impaired. On the other hand, some of these devices work in noisy surroundings, and this has the effect that this industrial noise can no longer be separated from the useful signal in the case of many of these devices. In such cases, it is necessary to obtain additional information on the ambient noise or the inner signals. For this purpose, the three signals can be used which are provided by a 3D accelerometer. The signals supplied by such a sensing element can be evaluated e.g. according to the very good filtering method according to Kalman. The three signals show phase delays between the three signals, the phase delays being caused by the sensing element, the physical dimensions of the workpiece and the sound velocity of the material of the workpiece.

The data recorded are converted into a spectral representation, e.g. by making use of a fast Fourier transform, so as to obtain the spectral response of the workpiece.

Subsequently, the spectral response calculated can be subjected to noise reduction processes, e.g. by means of accumulation of the data obtained and by means of special filtering methods (e.g. according to Prony or Pisarenko).

All workpieces have a resonant behavior and a non-resonant behavior depending on the excitation frequency. Resonant amplitudes have a maximum level at resonant frequencies which can be different for each individual workpiece. In FIG. 1a, the vibration amplitude of the workpiece is plotted along the vibration frequency. The curve represented shows a maximum at $f_{resonance}$. As far as the frequencies A and B are concerned, FIGS. 1b and 1c show which excitation force results in which deformation of the workpiece. The area lying between the two curves corresponds to the energy taken up by the workpiece. Since the areas enclosed by the curves in FIGS. 1b and 1c are largest in the vicinity of the resonant frequency, this is also the region which is most suitable for transmitting energy into the workpiece. The frequencies used for stress-relieving the workpiece must be chosen from the frequencies having maximum amplitude values in the response behavior during the test phase. The respective amplitude can be calculated on the basis of the measured acceleration with the aid of the following formula $$\hat{x} = \frac{\hat{a}}{\omega^2}$$

wherein $\hat{x}$ is the amplitude, $\hat{a}$ the acceleration measured, and $\omega$ the excitation frequency.

It is, however, possible that the excitation frequency determined with the aid of the measured curve originated from defects, faulty materials or mechanical resonant frequencies of individual parts of the workpiece. Such resonances are based on a negative damping factor or on a self-exciting vibration. These frequencies are not suitable for stress-relieving the workpiece. For differentiating between a resonance of this type and a resonance which is suitable for stress-relieving the workpiece, the variation of the vibration amplitude in the case of a varying excitation frequency during the test phase is evaluated. It is shown how a hard spring behavior, in FIG. 2a, and a soft spring behavior, in FIG. 2b, differ when the excitation frequency increases and decreases. The resonances which are not suitable for stress relief show a hard spring behavior, whereas the resonance ranges suitable for stress relief are characterized by a soft spring behavior. Both resonance ranges show characteristic amplitude jumps whose position and size vary depending on the behavior in question. When the behavior is a hard spring behavior, a big amplitude jump 1–2 takes place from a high amplitude 1 to a low amplitude 2 in the case of increasing excitation frequencies at a frequency lying above the center frequency, and a small amplitude jump 3–4 takes place from a lower amplitude 3 to a higher amplitude 4 in the case of decreasing excitation frequencies at a frequency lying below the frequency of the big amplitude jump and corresponding approximately to the center frequency. When the behavior is a soft spring behavior, a small amplitude jump 3–4 takes place from a smaller amplitude 3 to a higher amplitude 4 in the case of increasing excitation frequencies at a center frequency of the resonance range, and a big amplitude jump 1–2 takes place from a high amplitude 1 to a low amplitude 2 in the case of decreasing frequencies at a frequency that is lower than the frequency of the small amplitude jump 3–4.

Since it is not always possible to distinguish unequivocally between hard spring behavior and soft spring behavior on the basis of the amplitude values measured and in view of the negative effects of an excitation frequency with hard spring behavior, the excitation frequencies should only have assigned thereto a soft spring behavior if they show such a soft spring behavior beyond all doubt.

When the test phase has been finished and when the curves measured in connection with the respective increasing and decreasing excitation frequencies (microscanning) have been evaluated, the resonance ranges and frequencies, respectively, that are chosen from all the possible resonance ranges and frequencies are only those with the aid of which the internal stresses can actually be eliminated.

Excitation frequencies showing a hard spring behavior are not used for stress-relieving the workpiece. These frequencies are, however, used for checking whether the selected excitation frequencies showing a soft spring behavior are perhaps harmonics or sub-harmonics of the hard spring frequencies. Soft spring frequencies representing an integer multiple or a divisor of a hard spring frequency are not used for excitation during the stress-relief phase either.

The spectral responses of the test phase ascertained are evaluated still further for judging the energy transmission efficiency for the elimination of internal stresses. This processing is based on the ratio between the energy taken up by the workpiece and the energy transmitted into the workpiece for excitation. The energy injected in the workpiece by the vibrator can be determined on the basis of the power which is consumed in the course of one rotation or which—in accordance with a different embodiment—is contained in the power of the signal picked up by the accelerometer.

The energy dissipated by the damper can be determined by the following formula:

$$\Delta W = \oint F \cdot dx$$

wherein $\Delta W$ stands for the energy taken up and f(x) corresponds to a mathematical simulation of the workpiece. The accuracy of the result depends on the accuracy of the mathematical simulation. For simulating a system which is not linearly damped, the equation according to Duffing can be used. For a less good but much simpler calculation, the following formulae can be used:

$$\Delta W = \Pi \cdot \omega \cdot c \cdot \hat{x}^2$$

wherein $\omega$ corresponds to the rotational frequency, c to the damping coefficient and $\hat{x}$ to the motion amplitude. The energy efficiency n can then be calculated in accordance with the following formula:

$$\eta = \frac{\hat{a}^2}{\omega \cdot a_{RMS}^2}$$

wherein $a_{RMS}$ corresponds to the root mean square value of the acceleration, $\hat{a}$ to the peak value of the acceleration, and $\eta$ to the energy efficiency. Such a calculation can also be carried out with the aid of very simple, non-digital evaluation means with the aid of the harmonic distortion factor. This factor is calculated in accordance with the following formula:

$$HD = \frac{\sqrt{\sum_{i=2}^{n-1} F\{a[i]\}^2}}{F\{a[1]\}}$$

wherein $F\{a[i]\}$ corresponds to the harmonic of the i-th order of the acceleration spectrum. The efficiency factors calculated according to this method are, however, not very expressive, since the energy injected in the workpiece by the vibrator is not taken into account in the calculation. Stress-relief efficiency values calculated in accordance with this method select suitable stress-relief frequencies merely on tho basis of the fact that a higher percentage of the high-frequency spectral range is excited.

A better approach to a calculation of the energy efficiency is the calculation of the THD values (total harmonics distortion). This value can be calculated for each individual excitation, i.e. for each preset revolution frequency, according to the following formula:

$$THD = \frac{\sqrt{\sum_{i=2}^{n-1} F\{a[i]\}^2}}{\sqrt{\sum_{i=1}^{n-1} F\{a[i]\}^2}}$$

wherein THD stands for the efficiency value, $F\{a[i]\}$ for the spectral amplitude of the respective $i^{th}$ harmonic of the basic excitation frequency (i=1), and n for the total number of frequencies of the workpiece measured for each excitation. With the aid of the efficiency values calculated in this way, it is very easy to find the best vibration frequencies for stress relief, since all the calculated THD values are smaller than 1. In addition, THD values take into account the broader excitation frequency range when a non-sinusoidal excitation force is used.

The THD values are calculated for all excitation revolution values lying within a specific range around the peak values of the measured curve. Each THD value indicates the stress-relief efficiency that can be achieved with the aid of the respective excitation revolution frequencies and the energy injected in this way directly or via the harmonics. The bandwidth of excitation revolution frequencies within which a THD value is calculated for each frequency is determined in dependence upon the amplitude in the curve measured. Preferably, the bandwidth is so broad that it includes amplitude values in the measured curve at which the amplitude decreased, in comparison with the peak value, to a value corresponding approximately to 0.7 times or $1/\sqrt{2}$ times the value of the maximum amplitude. For each excitation revolution frequency ascertained on the basis of the measured curve, a corresponding frequency range can be determined. The mean THD values, which are calculated for each of these frequency ranges, are sorted in a descending sequence. In order to make the calculating operations less complicated, it is also possible to use only the THD values corresponding to the excitation revolution frequencies ascertained. The list of the THD values sorted according to size is then checked so as to find out whether an excitation revolution frequency of a THD value is a harmonic or sub-harmonic of another THD value. If one of the excitation frequencies corresponds to an integer multiple of another one, only the excitation frequency having assigned thereto the larger (mean) THD value will be taken into account when the process is being continued.

A THD value indicates to what extent an excitation frequency is capable of injecting vibrations into the workpiece in a frequency range suitable for stress relief. Hence, THD values will also be referred to as energy efficiency values hereinbelow.

The stress relief of the workpiece is then performed only with the aid of the frequencies having the highest THD values; the sequence of frequencies used for stress relief corresponds to the sequence ascertained.

All operations for operating a vibration machine for stress relieving a workpiece, especially the determination of suitable excitation frequencies, are preferably carried out with the aid of digital calculating machines.

In the course of a macroscanning run in the test phase also microscanning is carried out, as has been described hereinbefore. In so doing, the revolution values within each microscanning revolution range are scanned several times for each macroscanning revolution value. In each of the scanning directions, i.e. in the respective direction of increasing and decreasing revolution values, the average of a plurality of measured values is formed for each amplitude value measured. Practical experience has shown that, due to statistical fluctuations of the measured values, an amplitude value diagram, which is to be used later on for differentiating between hard and soft spring behaviors, should not be formed an the basis of a single microscanning run but on the basis of a superposition of a plurality of microscanning runs carried out in the same direction so as to make the amplitude value diagram more expressive. The values measured in this way can be used for obtaining an additional selection criterion for determining suitable excitation frequencies for stress relieving the workpiece. A prerequisite for this is that, as is common practice, the excitation in the test phase is carried out with the same amplitude, i.e. with the same eccentric, as in the subsequent stress relief phase. For this purpose, the resonant amplitude ascertained during the microscanning runs and the variance of the resonant amplitude are determined during the test phase. In this connection, it is of special interest whether the resonant amplitude varies during the microscanning. A variation of the resonant amplitude indicates to what extent the respective excitation frequency is capable of rapidly reducing internal stresses. Excitation frequencies causing changes in the resonant amplitude already in the course of the microscanning runs of the test phase are particularly suitable for fast stress relief. Each resonant frequency can have associated therewith a variance value. On the basis of the variance value ascertained for each resonant frequency, a list of ranks of the resonant frequencies can be determined, the frequencies having particularly high variance values being particularly suitable for a fast reduction of internal stresses.

In accordance with the method described hereinbefore, an energy efficiency value (THD value) as well as a variation efficiency value can be determined with regard to each selected revolution value (with maximum values of the vibration amplitude). Each of these values indicates for one of the two quality criteria the individual properties of each frequency. An overall quality criterion is, however, only obtained when the two individual criteria are combined, i.e. only revolution values having a high efficiency according to both criteria are particularly suitable for stress relief. Hence, a general efficiency value can only be indicated if both efficiency values are connected with one another in a mutually enhancing manner. This means that an increase in one of the two efficiency values must also result in a corresponding increase in a common efficiency value. Suitable connections are therefore e.g. a multiplication or an addition. A suitable common efficiency value, which is adapted to be used for selecting the stress relief frequencies, could be calculated e.g. according to the formula following hereinbelow:

$$E = THD \cdot \frac{\sigma}{m}$$

wherein: $E$—is the measured efficiency value, $THD$—is the calculated energy efficiency value, $\sigma$—is the variance value, $m$—is the resonant amplitude, and $\frac{\sigma}{m}$—is the variation efficiency value.

During the vibration used for stress relieving the workpiece, the excitation frequency scans a frequency range associated with the respective peak value. The bandwidth of this frequency range corresponds preferably to the bandwidth used for calculating the mean efficiency value. It follows that the workpiece is not only excited at a special frequency but a frequency range around the mean angular velocity is also scanned in the case of an intended constant number of revolutions per unit time. This has the effect that the workpiece is excited with a much broader frequency spectrum. For exciting the workpiece, eccentric vibrators are preferably used, which are capable of injecting more energy into the workpiece. A continuous scanning of frequencies around the selected resonant frequency causes an enlargement of the width of the injected spectrum in the case of a sinusoidal as well as in the case of a non-sinusoidal, e.g. rectangular excitation. By selecting the kind of excitation, the spectrum injected can be determined precisely.

For accelerating stress relief of a workpiece, it is also possible to use two vibrators at the same time. In so doing, these vibrators can either be operated with the same excitation frequency so as to increase the amount of energy injected or they can be operated at (slightly) different frequencies.

Summarizing, it can be stated that the described method of operating a vibration machine for stress relieving a workpiece comprises the operating steps following hereinafter. The workpiece is first caused to vibrate by means of a non-sinusoidal excitation force in a test phase, the excitation frequency fluctuating around an average value. At the same time, the vibration behavior of the workpiece is measured and evaluated. The excitation frequencies at which the workpiece exhibits peak values in the vibration behavior measured are fundamentally suitable for an excitation for stress relieving the workpiece. In a next step, these excitation frequencies must, however, be differentiated so as to find out which of these frequencies are capable of effecting a real reduction of internal stresses. For this purpose, the measured vibration behavior is evaluated in the range of the excitation frequencies selected ($f_1 \ldots f_n$) in the case of increasing and decreasing frequency values so as to be able to differentiate between a soft spring behavior and a hard spring behavior. For the remaining frequency values exhibiting a soft spring behavior, efficiency values (THD) are determined within a selected range around the peak values of the measured curve, the efficiency values being indicative of the efficiency with which energy is transmitted into the frequency range of interest in the case of the respective excitation frequency. A mean efficiency value is determined for each of the excitation frequency values that remained after the differentiation between hard spring behavior and soft spring behavior, the mean efficiency value being determined on the basis of the respective frequency range examined. Hence, each of the possible excitation frequency values has assigned thereto an efficiency value. At the same time, a variation efficiency value is determined which indicates to what extent an excitation frequency is capable of rapidly reducing internal stresses. Subsequently, a new, common efficiency value is determined for each of the excitation frequencies on the basis of both efficiency values.

Following this, a table is formed in which the common efficiency values are sorted according to size. In a further column of the table, the excitation frequencies corresponding to each efficiency value are listed. In this way, a list of ranks of suitable excitation frequencies is produced in which the excitation frequencies are arranged such that those at the beginning of this list of ranks are most suitable for exciting frequencies causing a reduction of internal stresses in the microscopic region of the workpiece. In a next step, the frequencies are selected which represent an integer multiple of some other excitation frequency of this list of ranks. Among these frequencies only the respective frequency having a higher efficiency value remains in the list of ranks.

The frequencies having the highest efficiency values are used for exciting the workpiece for relieving internal stresses. When the workpiece is caused to vibrate, a non-sinusoidal periodic force is preferably used for excitation and, in addition, the excitation frequency is varied around a mean value so that changes of the ideal excitation frequency resulting from an increasing reduction of internal stresses are, among other things, also taken into account in this way. In an ideal case, the vibration behavior of the workpiece will also be measured during the stress relief phase. The evaluation of the vibration behavior permits the stress relief process with a specific excitation frequency to be discontinued as soon as the evaluation of the measured vibration behavior shows that a predetermined stress relief value has been achieved.

In most cases, it will suffice to limit the stress relief of the workpiece to the three frequencies resulting in the highest THD values and efficiency values, respectively. It may happen that the fourth efficiency value differs only insignificantly from the third one. In this case, the workpiece should, as a precaution, also be stress relieved at the frequency assigned to the fourth THD value. Also this approach can be executed automatically in a very simple manner making use of a computer by forming the root mean square of the first three efficiency values and by comparing the root mean square with the fourth efficiency value. If the fourth efficiency value lies under a predetermined percentage of e.g. 50% of this root mean square, the selection can be limited to the first three frequencies. If the fourth efficiency value lies, however, above this threshold value, the fourth frequency should be used as well. This calculation can be extended to the next efficiency values following in the sequence of efficiency values until the given threshold value criterion has been fulfilled.

When a stress relief at the first three selected excitation frequencies has been carried out, it is advisable to carry out new test runs and to draw up a new table containing the respective efficiency values. On the basis of the differences between the values inserted in the old and in the new table, conclusions can be drawn with regard to the stress relief that has already taken place. In addition, three new excitation frequencies are obtained from the table that has now been drawn up; these three new excitation frequencies can be used for a new run for optimizing the stress relief still further. When there are no longer any substantial deviations between the values of two successive tables, it can be assumed that the workpiece has been stress relieved to a sufficient extent and that the process can be discontinued.

Although the present invention has been described with reference to a presently preferred embodiment, it will be appreciated by those skilled in the art that various modifications, alternatives, variations, etc., may be made without departing from the spirit and scope of the invention as defined in the appended claims.

What is claimed:

1. A method of operating a machine for stress relieving a workpiece, comprising the steps of:

using at least one vibrator to excite a workpiece during a test phase;

measuring the vibrational behavior of said workpiece in a limited operating range, said step of measuring the vibrational behavior resulting in a measured curve;

making a first selection of revolution values of said vibrator, based on said measured curve, resulting in said revolution values having maximum values of vibration amplitude;

determining an energy efficiency value for each of said revolution values, from said first selection, according to the equation:

$$THD = \frac{\sqrt{\sum_{i=2}^{n-1} F\{a[i]\}^2}}{\sqrt{\sum_{i=1}^{n-1} F\{a[i]\}^2}}$$

wherein

THD=energy efficiency value,

F{a[i]}=spectral amplitude value of the respective $i^{th}$ harmonic of the basic excitation frequency (i=1), and n=total number of frequencies of the workpiece measured for each excitation;

correlating said revolution values from said first selection with said energy efficiency values;

making a second selection of revolution values corresponding to the revolution values from said first selection having the highest said energy efficiency values; and subjecting said workpiece to said vibrations with revolution values resulting from said step of making a second selection.

2. A method of operating a machine for stress relieving a workpiece, as claimed in claim 1, wherein:

two revolution values are selected in said step of making a first selection;

a first of said two revolution values is an integer multiple of a second of said two revolution values; and only the revolution value of said two revolution values having a higher efficiency value is selected in said step of making a second selection.

3. A method of operating a machine for stress relieving a workpiece, as claimed in claim 1, further comprising the step of:

determining a mean energy efficiency value for each of said revolution values resulting from said step of making a first selection, wherein said mean energy efficiency values are based on revolution values in a specific range around said each of said revolution values resulting from said step of making a first selection, said range limited by respective upper and lower revolution values, wherein vibration amplitudes of said upper and lower revolution values are smaller than a respective maximum value by a specific value, said amplitudes of said upper and lower revolution values in said measured curve being smaller than said respective maximum value by a factor of $1/\sqrt{2}$.

4. A method of operating a machine for stress relieving a workpiece, as claimed in claim 1, further comprising the step of varying, in a stress relief phase, said revolution values from said step of making a second selection within a specific range around each of said revolution values from said step of making a second selection, said range being limited by respective upper and lower revolution values, wherein the vibration amplitudes of said upper and lower revolution values in said measured curve being smaller than the respective maximum value by a factor of $1/\sqrt{2}$.

5. A method of operating a machine for stress relieving a workpiece, as claimed in claim 1, further comprising the step of varying said revolution values in said test phase within a predetermined range around a respective number of excitation revolutions, continuously or in small steps, wherein a variation range is approximately 1% of an operating range used.

6. A method of operating a machine for stress relieving a workpiece, as claimed in claim 5, wherein said step of varying said revolution values is carried out a plurality of times, and wherein an average of the measured amplitude values is formed for each number of excitation revolutions in a direction of increasing and decreasing numbers of excitation revolutions.

7. A method of operating a machine for stress relieving a workpiece, as claimed in claim 6, further comprising the steps of:

determining, in said test phase, a variance of a resonant amplitude for each maximum value;

determining a variation efficiency value on the basis of the variance ascertained for each maximum value, said variation efficiency value being determined by forming the quotient of the variance and the resonant amplitude; and forming a common efficiency value by combining, for each maximum value, in a mutually enhancing manner, said energy efficiency value and a capability of a revolution value to rapidly reduce internal stresses in said workpiece.

8. A method of operating a machine for stress relieving a workpiece, as claimed in claim 7, wherein said step of forming a common efficiency value conforms to the equation:

$$E = THD \cdot \frac{\delta}{m}$$

wherein,

E=measured efficiency value;

THD=calculated energy efficiency value;

δ=variance value;

m=resonant amplitude; and

δ/m=variation efficiency value.

9. A method of operating a machine for stress relieving a workpiece, as claimed in claim 1, wherein said workpiece is excited by a non-sinusoidal periodic force in said test phase.

10. A method of operating a machine for stress relieving a workpiece, as claimed in claim 5, further comprising the step of evaluating, during the test phase, the measured curve, in a range of the revolution values selected for stress relieving the workpiece, to determine whether the workpiece exhibits a soft spring behavior or a hard spring behavior, wherein the revolution values exhibiting a hard spring behavior are not used for stress relieving the workpiece.

11. A method of operating a machine for stress relieving a workpiece, as claimed in claim 8, further comprising the step of determining whether a revolution value exhibiting a soft spring behavior is an integer multiple or divisor of another revolution value exhibiting a hard spring behavior, wherein said revolution values exhibiting a soft spring behavior are not used for stress relieving the workpiece.

12. A method of operating a machine for stress relieving a workpiece, as claimed in claim 10, further comprising the step of:

differentiating between a soft spring behavior and a hard spring behavior of the workpiece, wherein:

a small amplitude increase in the case of decreasing revolution frequencies and a large amplitude decrease in the case of increasing revolution frequencies indicates a hard spring behavior; and a large amplitude decrease in the case of decreasing revolution frequencies and a small amplitude increase in the case of increasing revolution frequencies indicates a soft spring behavior.

13. A method of operating a machine for stress relieving a workpiece, as claimed in claim 10, further comprising the step of:

differentiating between a soft spring behavior and a hard spring behavior of the workpiece, wherein:

a large amplitude decrease occurring at a revolution frequency above that of a smaller amplitude increase indicates a hard spring behavior; and a large amplitude decrease occurring at a revolution frequency below that of said smaller amplitude increase indicates a soft spring behavior.

14. A method of operating a machine for stress relieving a workpiece, as claimed in claim 10, wherein a revolution value is determined as having a hard spring behavior if a soft spring behavior cannot be determined for said revolution value with certainty.

15. A method of operating a machine for stress relieving a workpiece, as claimed in claim 14, wherein said workpiece is excited by a non-sinusoidal periodic force in said test phase.

16. A method of operating a machine for stress relieving a workpiece, as claimed in claim 1, wherein two vibrators are used for stress relieving said workpiece with the revolution values resulting from said step of making a second selection, said vibrators operating with slightly different numbers of excitation revolutions.

17. A method of operating a machine for stress relieving a workpiece, as claimed in claim 1, further comprising the step of:

measuring the vibratory behavior of said workpiece during the stress relief phase;

evaluating a result of said step of measuring the vibratory behavior during the stress relief phase so as to cause the workpiece to vibrate only as long as is necessary for achieving a predetermined degree of stress relief, with one of the selected revolution frequencies being discontinued as soon as the measured vibration behavior has reached a predetermined degree of symmetry a predetermined degree of flatness in the range of the respective resolution frequency.

* * * * *

UNITED STATES PATENT AND TRADEMARK OFFICE
CERTIFICATE OF CORRECTION

PATENT NO : 6,116,088
DATED : September 12, 2000
INVENTOR(S) : Dietmar Schneider and Christian Vava It is certified that error appears in the above-identified patent and that said Letters Patent is hereby corrected as shown below:

Column 15, line 15, delete "said" and insert --a--.

Column 16, line 20, after "symmetry" insert --and-- .

Signed and Sealed this

First Day of May, 2001

NICHOLAS P. GODICI

*Attest:*

*Attesting Officer*        Acting Director of the United States Patent and Trademark Office